United States Patent
O'Brien et al.

(10) Patent No.: US 11,555,810 B2
(45) Date of Patent: *Jan. 17, 2023

(54) SPECTROSCOPIC CLASSIFICATION OF CONFORMANCE WITH DIETARY RESTRICTIONS

(71) Applicant: VIAVI Solutions Inc., San Jose, CA (US)

(72) Inventors: Nada A. O'Brien, Santa Rosa, CA (US); Changmeng Hsiung, Redwood City, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 1 day.

This patent is subject to a terminal disclaimer.

(21) Appl. No.: 16/949,871

(22) Filed: Nov. 18, 2020

(65) Prior Publication Data

US 2021/0072212 A1    Mar. 11, 2021

Related U.S. Application Data

(63) Continuation of application No. 16/587,260, filed on Sep. 30, 2019, now Pat. No. 10,852,285, which is a
(Continued)

(51) Int. Cl.
*G06F 11/30* (2006.01)
*G01N 33/12* (2006.01)
(Continued)

(52) U.S. Cl.
CPC ............ *G01N 33/12* (2013.01); *G01N 21/27* (2013.01); *G06K 9/6228* (2013.01); *G06K 9/6269* (2013.01); *G06V 30/242* (2022.01)

(58) Field of Classification Search
CPC ..................................................... G01N 33/12
See application file for complete search history.

(56) References Cited

U.S. PATENT DOCUMENTS

| | | |
|---|---|---|
| 5,349,189 A | 9/1994 | Maggard |
| 5,912,114 A | 6/1999 | Hutchinson et al. |
| | (Continued) | |

FOREIGN PATENT DOCUMENTS

| | | |
|---|---|---|
| CN | 104185850 A | 12/2014 |
| EP | 2081012 A1 | 7/2009 |
| | (Continued) | |

OTHER PUBLICATIONS

Diffen, "Halal vs. Kosher," http://www.diffen.com/difference/HalaivsKosher, Jan. 17, 2014, 5 pages.
(Continued)

*Primary Examiner* — Phuong Huynh
(74) *Attorney, Agent, or Firm* — Harrity & Harrity, LLP (57) ABSTRACT

A device may receive a classification model generated based on a set of spectroscopic measurements performed by a first spectrometer. The device may store the classification model in a data structure. The device may receive a spectroscopic measurement of an unknown sample from a second spectrometer. The device may obtain the classification model from the data structure. The device may classify the unknown sample into a Kosher or non-Kosher group or a Halal or non-Halal group based on the spectroscopic measurement and the classification model. The device may provide information identifying the unknown sample based on the classifying of the unknown sample.

20 Claims, 9 Drawing Sheets

Related U.S. Application Data continuation of application No. 15/401,669, filed on Jan. 9, 2017, now Pat. No. 10,444,213.

(60) Provisional application No. 62/379,605, filed on Aug. 25, 2016.

(51) Int. Cl.
  G06K 9/62 (2022.01)
  G06V 30/242 (2022.01)
  G01N 21/27 (2006.01)

(56) References Cited

U.S. PATENT DOCUMENTS

| | | | |
|---|---|---|---|
| 9,362,886 | B2 | 6/2016 | Takebayashi et al. |
| 10,444,213 | B2 | 10/2019 | O'Brien et al. |
| 10,852,285 | B2 * | 12/2020 | O'Brien .............. G06V 30/242 |
| 10,936,967 | B2 | 3/2021 | Tsuchida et al. |
| 2002/0090664 | A1 | 7/2002 | Wiegand et al. |
| 2010/0287125 | A1 | 11/2010 | Okubo |
| 2015/0051840 | A1 | 2/2015 | Vervier et al. |
| 2016/0109423 | A1 | 4/2016 | Reichl et al. |
| 2016/0140870 | A1 * | 5/2016 | Connor .............. G09B 19/0092 356/51 |
| 2016/0171514 | A1 * | 6/2016 | Frank .................... G06Q 30/02 705/7.29 |

FOREIGN PATENT DOCUMENTS

| | | |
|---|---|---|
| JP | H07282078 A | 10/1995 |
| JP | H11190736 A | 7/1999 |
| JP | 2004226257 A | 8/2004 |
| JP | 2006507504 A | 3/2006 |
| JP | 2009524008 A | 6/2009 |
| JP | 2009532708 A | 9/2009 |
| JP | 2009282685 A | 12/2009 |
| JP | 2012122851 A | 6/2012 |
| JP | 2015516570 A | 6/2015 |
| JP | 2016052083 A | 4/2016 |
| WO | 2004048929 A2 | 6/2004 |
| WO | 2007064964 A2 | 6/2007 |
| WO | 2007115296 A2 | 10/2007 |
| WO | 2016084326 A1 | 6/2016 |

OTHER PUBLICATIONS

Extended European Search Report for Application No. EP17187826, dated Dec. 7, 2017, 13 pages.

Extended European Search Report for Application No. EP17187826, dated Feb. 26, 2018, 15 pages.

Grandin T., et al., "Religious Slaughter and Animal Welfare: A Discussion for Meat Scientists," Meat Focus International, http://www.gradin.com/ritual/kosher.slaugh.html, Mar. 1994, 12 pages.

Mansor T.S.T., et al., "Application of Fast Gas Chromatography and Fourier Transform Infrared Spectroscopy for Analysis of Lard Adulteration in Virgin Coconut Oil," Food Analytical Methods, Oct. 2010, vol. 4 (3), XP019932580, pp. 365-372.

Meat Science, "Kosher and Halal,"http://meat.tamu.edu/ansu-307-honors/Kosher-Halal/, Oct. 2, 2013, 9 pages.

Nur Azira T., et al., "Differentiation of Bovine and Porcine Gelatins in Processed Products via Sodium Dodecyl Sulphate-Polyacrylamide Gel Electrophoresis (SDS-PAGE) and Principal Component Analysis (PCA) Techniques," International Food Research Journal, vol. 19(3), 2012, pp. 1175-1180.

Pederson C.G., et al., "Pocket-Size Near-Infrared Spectrometer for Narcotic Materials Identification," Proceedings of SPIE, May 2014, vol. 9101, XP060037578, pp. 91010O-1-91010O-11.

Rohman A., et al., "Analysis of Pork Adulteration in Beef Meatbail Using Fourier Transform Infrared (FTIR) Spectroscopy," Meat Science, Elsevier Science, Dec. 2010, vol. 88(1), XP028129889, 5 pages.

Schmutzler M., et al., "Methods For Detection of Pork Adulteration in Veal Products Based on FT-NIR Spectroscopy for Laboratory, Industrial and On-site Analysis," Food Control, Elsevier Science,, Nov. 2015, vol. 57, 10 pages.

Wikipedia, "Machine Learning", Nov. 2018, 1 page [retrieved on Dec. 26, 2019] Retrieved from the internet [URL: https://en.wikipedia.org/w/index.php?title=Machine_learning&oldid=871390169].

Xu L., et al., "Rapid Discrimination of Pork in Halal and non-Halal Chinese Ham Sausages by Fourier Transform Infrared (FTIR) Spectroscopy and Chemometrics", MeatScience, Dec. 2012, vol. 92, pp. 506-510.

Motoyama., "Special Feature: Halal Science, Halal Science of Meat and Possibility of Non-destructive Detection of Lard Using Spectroscopy," Bioindustry, Apr. 12, 2016, vol. 33 (4), pp. 33-37.

Rfriend Tistory., "[R Machine Learning] How to Avoid Over-fitting? (Training vs. Validation vs. Test Set), May 2016, pp. 1-6, Retrieved from the Internet: [URL:" >https://rfriend.tistory.com/188] [retrieved on Mar. 7, 2022].

* cited by examiner

SPECTROSCOPIC CLASSIFICATION OF CONFORMANCE WITH DIETARY RESTRICTIONS

RELATED APPLICATIONS

This application is a continuation of U.S. patent application Ser. No. 16/587,260, filed on Sep. 30, 2019 (now U.S. Pat. No. 10,852,285), which is a continuation of U.S. patent application Ser. No. 15/401,669, filed on Jan. 9, 2017 (now U.S. Pat. No. 10,444,213), which claims priority under 35 U.S.C. § 119 to U.S. Provisional Patent Application No. 62/379,605, filed on Aug. 25, 2016, the contents of which are incorporated by reference herein in its their entirety.

BACKGROUND

Raw material identification may be utilized for quality-control of pharmaceutical products, to determine a type of unknown chemical, or the like. For example, raw material identification may be performed on a compound to determine whether component ingredients of the compound correspond to a packaging label associated with the compound. Spectroscopy may facilitate non-destructive raw material identification (RMID) with reduced preparation and data acquisition time relative to other chemistry techniques.

Some people may abide by dietary restrictions relating to a tradition or a religion. For example, some Jewish people may desire to eat only foods that have been deemed Kosher in accordance with Jewish law. Similarly, some Muslim people may desire to eat only foods that have been deemed Halal in accordance with Islamic law. Additionally, many other people may follow other dietary restrictions relating to a tradition, a religion, an ethical code, or the like. A feature of both Kosher certification (i.e., designation of a food item as Kosher) and Halal certification (i.e., designation of a food item as Halal) is conformance with laws regarding the slaughter of animals. For example, both Judaic ritual slaughter (Shechita) and Islamic ritual slaughter (Zabihah) require an animal to be cut across the neck with a non-serrated blade in a single clean attempt to sever main blood vessels of the animal, and to drain the blood of the animal.

SUMMARY

According to some possible implementations, a device may include one or more processors. The one or more processors may receive information identifying a result of a spectroscopic measurement of an unknown sample. The one or more processors may perform one or more classifications of the unknown sample to classify the unknown sample into a particular group based on the result of the spectroscopic measurement and one or more classification models. The one or more classification models may use a support vector machine (SVM) classifier technique. The one or more classification models may relate to a set of groups including the particular group. A first subset of the set of groups may be a first meta-group including the particular group. A second subset of the set of groups may be a second meta-group not including the particular group. The one or more processors may provide information indicating a classification of the unknown sample into the first meta-group based on performing the one or more classifications of the unknown sample to classify the unknown sample into the particular group.

According to some possible implementations, a non-transitory computer-readable medium may store one or more instructions that, when executed by one or more processors, cause the one or more processors to receive information identifying a spectrum of an unknown sample analyzed by a spectrometer. The one or more instructions, when executed by the one or more processors, may cause the one or more processors to perform a first classification of the unknown sample based on the spectrum of the unknown sample and a global classification model. The global classification model may be associated with a support vector machine (SVM) classifier technique. The global classification model may include a plurality of groups. The one or more instructions, when executed by the one or more processors, may cause the one or more processors to generate a local classification model based on a result of the first classification of the unknown sample. The one or more instructions, when executed by the one or more processors, may cause the one or more processors to perform a second classification of the unknown sample based on the spectrum of the unknown sample and the local classification model. The one or more instructions, when executed by the one or more processors, may cause the one or more processors to provide information identifying a meta-group to which the unknown sample is classified based on the local classification model. The meta-group may include a subset of the plurality of groups.

According to some possible implementations, a method may include receiving, by a device, a classification model generated based on a set of spectroscopic measurements performed by a first spectrometer. The method may include storing, by the device, the classification model in a data structure. The method may include receiving, by the device, a spectroscopic measurement of an unknown sample from a second spectrometer. The method may include obtaining, by the device, the classification model from the data structure. The method may include classifying, by the device, the unknown sample into a Kosher or non-Kosher group or a Halal or non-Halal group based on the spectroscopic measurement and the classification model. The method may include providing, by the device, information identifying the unknown sample based on the classifying of the unknown sample.

DETAILED DESCRIPTION

The following detailed description of example implementations refers to the accompanying drawings. The same reference numbers in different drawings may identify the same or similar elements.

Many people abide by dietary restrictions relating to a manner in which animals are prepared for consumption. For example, in both Jewish tradition and in Islamic tradition, animals are required to be slaughtered using a cut across the neck with a non-serrated blade in a single clean attempt to sever main blood vessels of the animal. Moreover, the animal must be drained of blood after the slaughter. Similarly, some traditions restrict a type of animal that may be consumed. For example, meat from a pig is neither Kosher nor Halal regardless of a method of slaughter. As another example, some Islamic traditions permit consumption of shellfish, but Jewish tradition does not permit consumption of shellfish.

Although meat may be certified as Kosher (i.e., allowed under the Jewish tradition) or Halal (i.e., allowed under the Islamic tradition), buyers may be unable to determine whether the meat was properly slaughtered based on visual inspection. Moreover, when consuming food at a restaurant, customers may be unable to view an inspection label affixed to packaging of meat prior to preparation of the meat. Furthermore, a customer may be unable to determine a type of animal from which the meat is derived based on visual inspection. This may result in a person who abides by a dietary restriction being hesitant to consume animal products.

Physical conditions and/or chemical conditions of an animal may be altered based on a type of slaughter. For example, cortisol levels of animals for which Kosher slaughter or Halal slaughter is performed may be different from cortisol levels of animals for which another type of slaughter is performed. Moreover, different types of meats obtained from different animals may be associated with physical differences and/or chemical differences. For example, proteins from pork meat of a pig may differ from proteins from beef meat of a cow. However, large amounts of variance may exist between different types of animals, different breeds of a particular type of animal, different cuts of meat of a particular animal, or the like. This may limit an effectiveness of comparing an unknown sample of meat to a set of known reference samples of meat.

Implementations, described herein, may provide a device (e.g., a spectrometer) that utilizes local classification modeling to identify an unknown sample based on a spectroscopic measurement of the unknown sample. In this way, a spectrometer may be utilized to determine whether an unknown sample corresponds to a Kosher type of meat, a Halal type of meat, or a type of meat that is neither Kosher nor Halal. In this way, a buyer or a consumer of meat can verify that meat being sold as or marketed as being Kosher or Halal is genuine. Moreover, by aggregating multiple classification groups (e.g., a Kosher beef flank steak, a Kosher beef strip steak, and a Kosher beef sirloin steak), for which relatively few samples are provided in a training set, into a meta-group (e.g., Kosher) to perform a classification (e.g., Kosher or non-Kosher), an accuracy of the classification is improved relative to attempting to perform a classification into a particular classification group.

Figure 1:
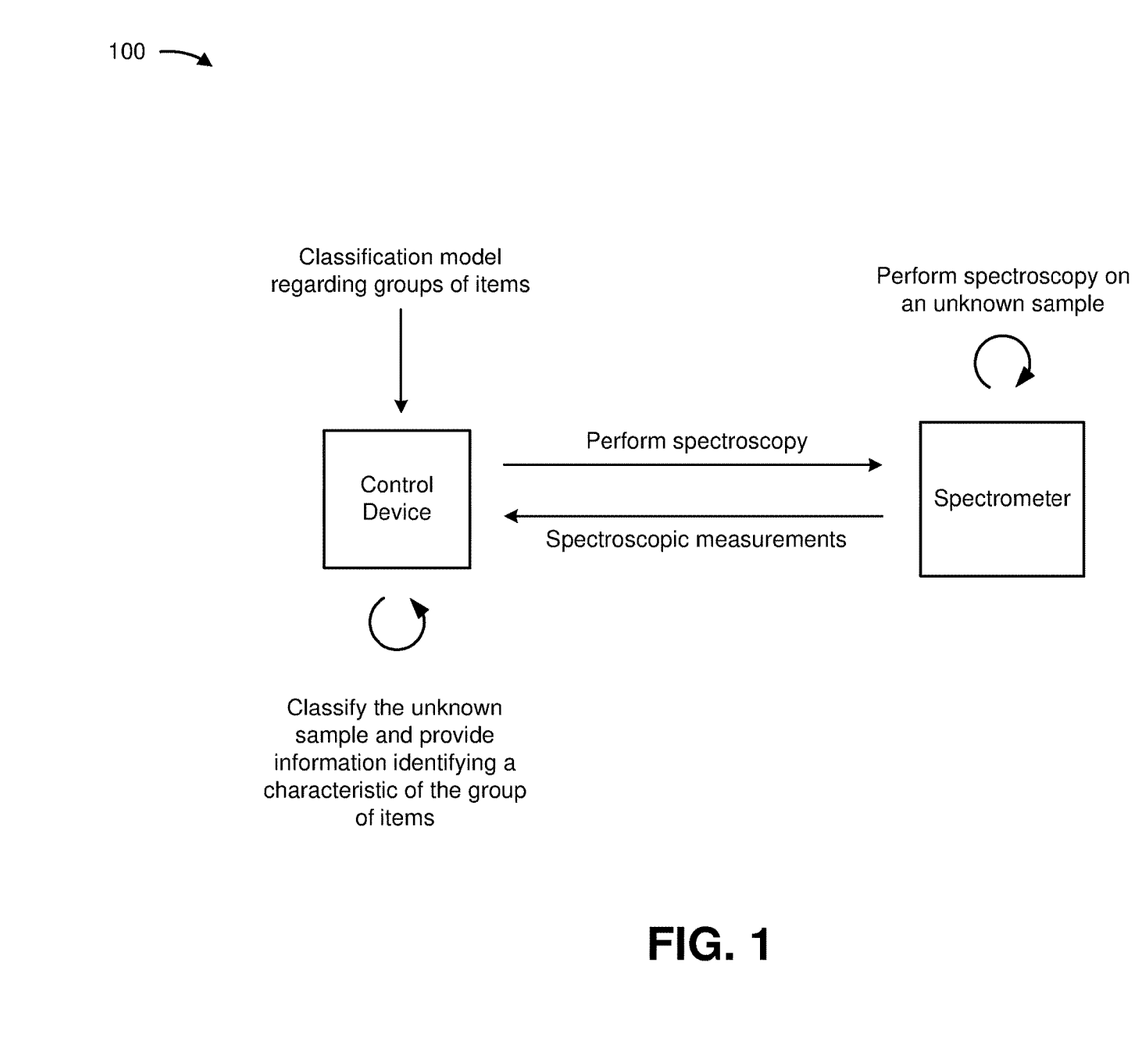
FIG. 1 is a diagram of an overview of an example implementation described herein.

FIG. 1 is a diagram of an overview of an example implementation 100 described herein. As shown in FIG. 1, example implementation 100 may include a control device and a spectrometer.

As further shown in FIG. 1, the control device may receive a classification model regarding groups of items. For example, the control device may receive a particular classification model for classifying items of food (e.g., meat) as Halal or non-Halal based on a spectroscopic measurement relating to a physical characteristic and/or a chemical characteristic of the item of food, such as a cortisol level of the item of food, a type of animal from which the item of food is derived, or the like. In another example, the control device may receive another classification model for classifying items of food as Kosher or non-Kosher. The particular classification model may be associated with aggregating multiple groups based on a common characteristic. For example, the classification model may be associated with aggregating a set of Halal groups (e.g., Halal beef strip streak and Halal beef flank steak or Halal chicken breast and Halal chicken thigh) or a set of non-Halal classes (e.g., non-Halal beef strip steak and non-Halal beef flank steak) into a set of meta-groups (e.g., Halal and non-Halal).

As further shown in FIG. 1, the control device may cause the spectrometer to perform spectroscopy on an unknown sample (e.g., an item of food, such as a packaged item of meat at a supermarket or a prepared dish at a restaurant). The control device may receive a set of spectroscopic measurements of the unknown sample based on causing the spectrometer to perform spectroscopy. For example, the control device may receive information identifying a spectrum of the unknown sample. In this case, the spectrum of the unknown sample may correspond to cortisol levels in the unknown sample, which may be different for Kosher or non-Kosher meat or for Halal or non-Halal meat, thus permitting a classification of the unknown sample. The control device may classify the unknown sample and may provide information identifying a characteristic of the group of items. For example, the control device may identify a meta-group of the unknown sample as Halal, and may provide information indicating that the sample is predicted to be Halal. In some implementations, the control device may generate a local classification model based on a global classification model, and may utilize the local classification model to classify the unknown sample. In some implementations, the control device may utilize a particular type of classifier.

In this way, a control device uses a classification model and results of spectroscopy to identify whether an unknown sample is associated with a particular characteristic (e.g., Kosher or Halal) of a meta-group of multiple classification groups. Moreover, based on utilizing a classification model associated with aggregating multiple groups based on the particular characteristic, the control device improves an accuracy of the classification relative to attempting to classify the unknown sample into an individual group.

As indicated above, FIG. 1 is provided merely as an example. Other examples are possible and may differ from what was described with regard to FIG. 1.

Figure 2:
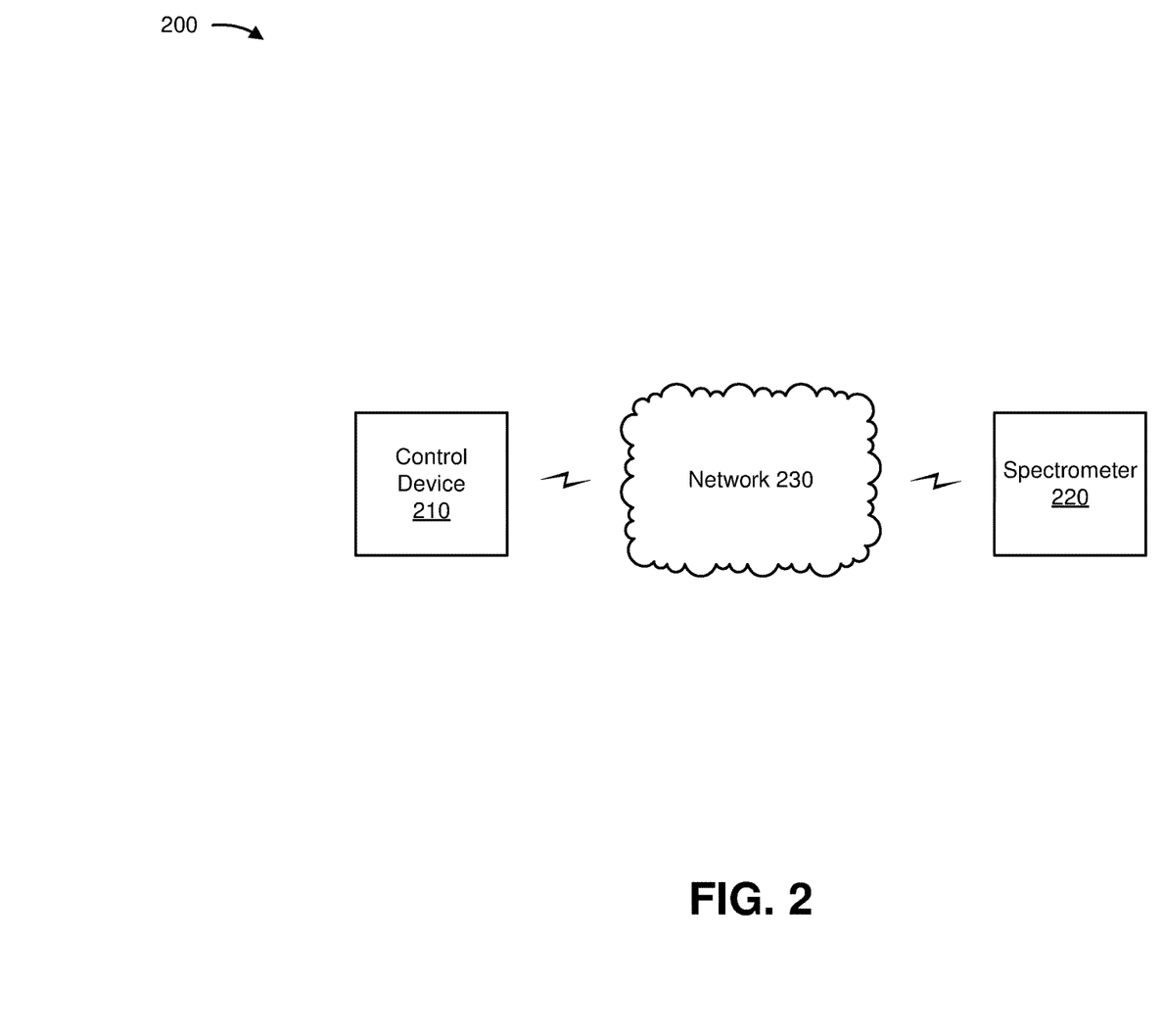
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a control device 210, a spectrometer 220, and a network 230. Devices of environment 200 may interconnect via wired connections, wireless connections, or a combination of wired and wireless connections.

Control device 210 includes one or more devices capable of storing, processing, and/or routing information associated with identifying an unknown sample based on a spectroscopic measurement. For example, control device 210 may include a server, a computer (e.g., a desktop computer, a laptop computer, or a tablet computer), a wearable device, a cloud computing device in a cloud computing environment, a mobile device, a smart phone, or the like that generates a classification model using a particular classifier and based on a set of spectroscopic measurements of a training set, and/or utilizes the classification model to identify an unknown sample. In some implementations, multiple control devices 210 may utilize a common classification model.

For example, a first control device 210 may generate the classification model and provide the classification model to a second control device 210, which may use the classification model to identify an unknown sample (e.g., at a restaurant, at a meat packaging plant, etc.). For example, control device 210 may utilize a support vector machine (SVM) type of classifier with a linear kernel, a radial basis function (rbf) kernel, or the like. In this case, control device 210 may perform a classification based on a confidence measure (wProb) technique, a decision value (DecVal) technique, or the like. In some implementations, control device 210 may be associated with a particular spectrometer 220. In some implementations, control device 210 may be associated with multiple spectrometers 220. In some implementations, control device 210 may receive information from and/or transmit information to another device in environment 200, such as spectrometer 220.

Spectrometer 220 includes one or more devices capable of performing a spectroscopic measurement on a sample. For example, spectrometer 220 may include a spectrometer device that performs spectroscopy (e.g., vibrational spectroscopy, such as near infrared (NIR) spectroscopy, mid-infrared spectroscopy (mid-IR), Raman spectroscopy, or the like). In some implementations, spectrometer 220 may be incorporated into a wearable device, such as a wearable spectrometer or the like. In some implementations, spectrometer 220 may be incorporated into a mobile device, such as a smart phone, a tablet computer, a laptop computer, or the like. In some implementations, spectrometer 220 may receive information from and/or transmit information to another device in environment 200, such as control device 210.

Network 230 may include one or more wired and/or wireless networks. For example, network 230 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. For example, although control device 210 and spectrometer 220 are described, herein, as being two separate devices, control device 210 and spectrometer 220 may be implemented within a single device. Additionally, or alternatively, a set of devices (e.g., one or more devices) of environment 200 may perform one or more functions described as being performed by another set of devices of environment 200.

Figure 3:
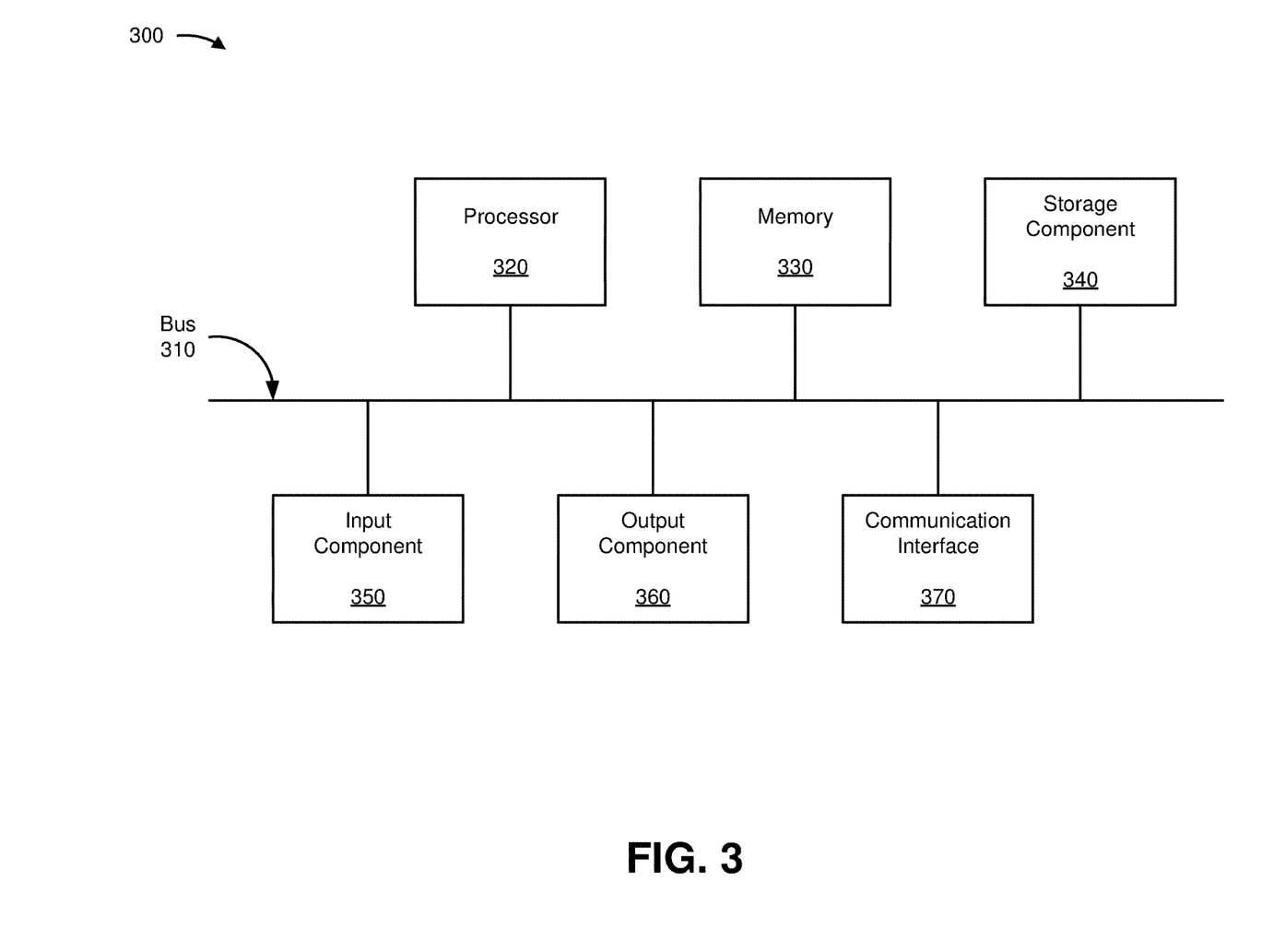
FIG. 3 is a diagram of example components of one or more devices of FIG. 2.

FIG. 3 is a diagram of example components of a device 300. Device 300 may correspond to control device 210 and/or spectrometer 220. In some implementations, control device 210 and/or spectrometer 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a central processing unit (CPU), a graphics processing unit (GPU), an accelerated processing unit (APU), a microprocessor, a microcontroller, a digital signal processor, a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
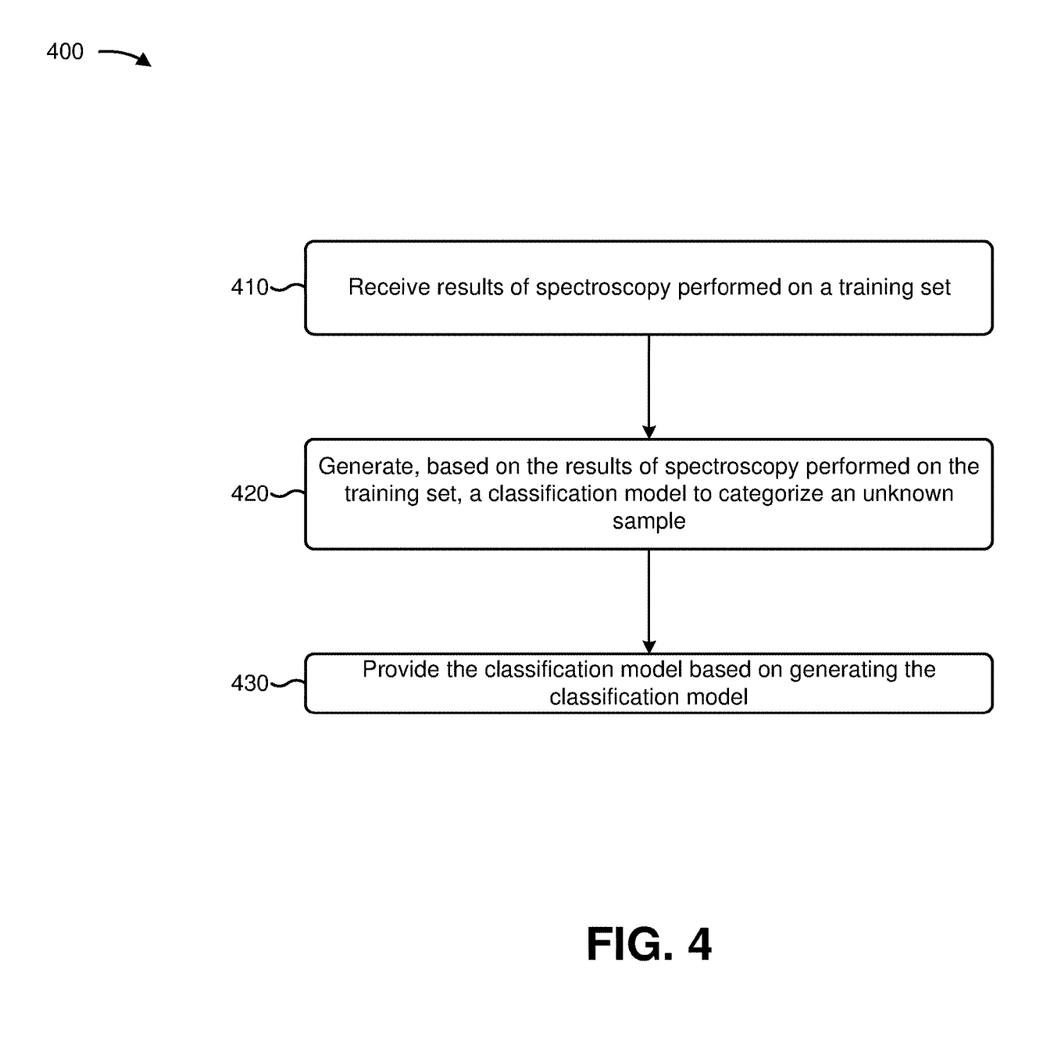
FIG. 4 is a flow chart of an example process for generating a classification model based on a training set.

FIG. 4 is a flow chart of an example process 400 for generating a classification model based on a training set. In some implementations, one or more process blocks of FIG. 4 may be performed by control device 210. In some implementations, one or more process blocks of FIG. 4 may be performed by another device or a group of devices separate from or including control device 210, such as spectrometer 220.

As shown in FIG. 4, process 400 may include receiving results of spectroscopy performed on a training set (block 410). For example, control device 210 may receive results of spectroscopy performed on the training set. The training set may refer to a set of samples of one or more known items, which are utilized to generate a classification model. For example, the training set may include one or more samples of a set of meats (e.g., a set of Kosher meats, a set of non-Kosher meats, a set of Halal meats, or a set of non-Halal meats) to control for local differences in a particular item of meat (e.g., a first cortisol level in a first sample of Kosher beef flank steak and a second cortisol level in a second sample of Kosher beef flank steak from a common source). In some implementations, the set of items may include multiple types of meat (e.g., beef, pork, chicken, etc.), multiple cuts of meat (e.g., flank, rib, breast, etc.), multiple preparations of meat (e.g., raw, seared, stewed, etc.), or the like to permit classification of unknown samples that a user may encounter.

In some implementations, the training set may be selected based on an expected set of items for which an identification is to be performed. For example, when an identification of an unknown sample is expected to be performed for Kosher beef and non-Kosher beef, the training set may include a set of samples of cuts of beef, breeds of cow, cooked beef and uncooked beef, or the like. In some implementations, the training set may be selected to include a particular quantity of samples for each type of meat. For example, the training set may be selected to include multiple samples (e.g., 5 samples, 10 samples, 15 samples, 50 samples, etc.) of a particular group of meat, such as Kosher hotdogs, non-Kosher hotdogs, or the like. In this way, control device 210 can be provided with a threshold quantity of spectra associated with a particular type of meat, thereby facilitating generation of a group, for a classification model (e.g., a global classification model or a local classification model), to which unknown samples can be accurately assigned.

However, based on a local variance in samples (e.g., in a common source, a common breed, a common cut of meat, a common type of animal), a threshold quantity of samples may be infeasible, and control device 210 may generate the classification model using fewer samples than the threshold quantity of samples. In this case, control device 210 may aggregate multiple groups to improve prediction accuracy relative to performing predictions using groups identified using fewer samples than the threshold quantity of samples.

Additionally, or alternatively, during configuration, testing may be performed of multiple classifier techniques to select a particular classifier technique associated with a threshold level of performance (e.g., a threshold prediction success rate) when performing predictions using a model trained on less than a threshold quantity of samples of a training set. For example, control device 210 may perform testing using a set of configuration parameters, such as using a linear kernel, an rbf kernel, a wProb confidence metric, a wDecVals confidence metric, or the like, and may select a particular combination of configuration parameters for subsequent use based on comparing performance of combinations of configuration parameters.

In some implementations, control device 210 may receive information identifying a set of spectra corresponding to samples of a training set. For example, control device 210 may receive information identifying a particular spectrum, which was observed when spectrometer 220 performed spectroscopy on the training set. Additionally, or alternatively, control device 210 may receive other information as results of the set of spectroscopic measurements. For example, control device 210 may receive information associated with identifying an absorption of energy, an emission of energy, a scattering of energy, or the like.

In some implementations, control device 210 may receive information identifying the results of the set of spectroscopic measurements from multiple spectrometers 220. For example, control device 210 may control for physical conditions, such as a difference between the multiple spectrometers 220, a potential difference in a lab condition, or the like, by receiving spectroscopic measurements performed by multiple spectrometers 220, performed at multiple different times, performed at multiple different locations, or the like.

As further shown in FIG. 4, process 400 may include generating, based on the results of spectroscopy performed on the training set, a classification model to categorize an unknown sample (block 420). For example, control device 210 may generate, based on the results of spectroscopy performed on the training set, the classification model to categorize the unknown sample.

In some implementations, control device 210 may generate a classification model associated with an SVM classifier technique based on information identifying the results of spectroscopy. SVM may refer to a supervised learning model that performs pattern recognition for classification. In some implementations, control device 210 may utilize a particular type of kernel function when generating the classification model using the SVM technique. For example, control device 210 may utilize an rbf (e.g., termed SVM-rbf) type of kernel function, a linear function (e.g., termed SVM-linear and termed hier-SVM-linear when utilized for a multi-stage classification technique) type of kernel function, a sigmoid function type of kernel function, a polynomial function type of kernel function, an exponential function type of kernel function, or the like. In some implementations, control device 210 may utilize a particular type of SVM, such as a probability value based SVM (e.g., classification based on determining a probability that a sample is a member of a class of a set of classes, such as wProb), a decision value based SVM (e.g., classification utilizing a decision function to vote for a group, of a set of groups, as being the group of which the sample is a member, such as DecVal or wDecVal), or the like.

In some implementations, control device 210 may generate the classification model based on information identifying samples of the training set. For example, control device 210 may utilize the information identifying the types of compounds represented by samples of the training set (e.g., types of items of food) to identify groups of spectra associated with types of compounds (e.g., groups associated with different animals, groups associated with different breeds of a particular type of animal, and/or groups associated with different cuts of meat).

In some implementations, control device 210 may train the classification model when generating the classification model. For example, control device 210 may cause the classification model to be trained using a portion of the results of spectroscopy. Additionally, or alternatively, control device 210 may perform an assessment of the classification model. For example, control device 210 may verify the classification model (e.g., for predictive strength) utilizing another portion of the results of spectroscopy.

In some implementations, control device 210 may validate the classification model when generating the classification model. For example, control device 210 may determine a metric relating to results of performing classification of a training set, such as a prediction success rate (sometimes termed a PSR or PS) value. In this case, control device 210 may test the classification model using a testing technique, such as a T-Odd/P-Even technique (e.g., odd numbered samples are selected as a training set for training the classification model, even numbered samples are selected as a prediction set for testing the classification model), a P-Odd/T-Even technique (e.g., odd numbered samples are selected as a prediction set for testing the classification model, even numbered samples are selected as a training set for training the classification model), a one sample out technique (e.g., for each sample selected as a single sample prediction set, each other sample is used as a training set), or the like. In some implementations, control device 210 may select a particular classifier technique based on the results of performing classification of the training set. For example, control device 210 may select to use a confidence value based selection technique, a decision value based selection technique, a local classification modeling based classification technique, or the like. In some implementations, control device 210 may select the particular classifier technique based on results of verifying a classification model, generated using the particular classifier technique and a training set, using a prediction set. Additionally, or alternatively, during manufacture, a particular classifier technique may be selected based on results of verifying the classification model.

As further shown in FIG. 4, process 400 may include providing the classification model based on generating the classification model (block 430). For example, control device 210 may provide the classification model based on generating the classification model. In some implementations, control device 210 may provide the classification model to other control devices 210 associated with other spectrometers 220 after generating the classification model. For example, a first control device 210 may generate the classification model and may load the classification model onto multiple second control devices 210 for utilization with multiple corresponding spectrometers 220. In this case, a particular second control device 210 may store the classification model, and may utilize the classification model in classifying one or more samples of an unknown set, as described herein with regard to FIG. 6. Additionally, or alternatively, control device 210 may store the classification model for utilization by control device 210 in classifying the one or more samples. In this way, control device 210 provides the classification model for utilization in identification of unknown samples.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
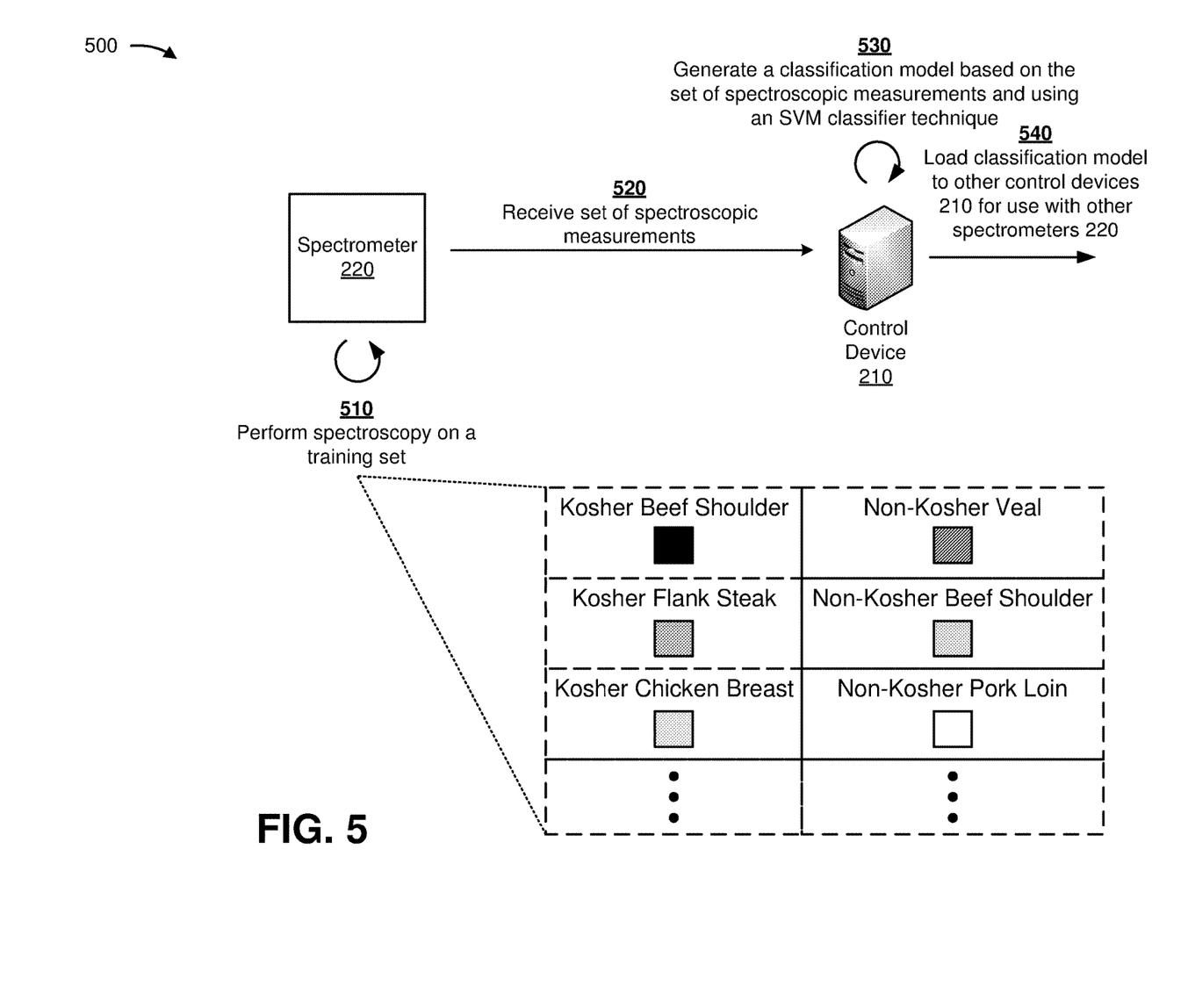
FIG. 5 is a diagram of an example implementation relating to the example process shown in FIG. 4.

FIG. 5 is a diagram of an example implementation 500 relating to example process 400 shown in FIG. 4. FIG. 5 shows an example of generating a classification model based on a training set.

As shown in FIG. 5, and by reference number 510, spectrometer 220 performs spectroscopy on a training set. For example, based on receiving a request to perform spectroscopy from control device 210, spectrometer 220 may determine a set of spectra for a set of samples (e.g., a Kosher Beef Shoulder sample, a Kosher Flank Steak sample, a Kosher Chicken Breast sample, a Non-Kosher Veal sample, a Non-Kosher Beef Shoulder sample, a Non-Kosher Pork Loin sample, or the like). As shown by reference number 520, control device 210 receives a set of spectroscopic measurements from spectrometer 220. For example, control device 210 may receive information identifying the set of spectra for the set of samples. As shown by reference number 530, control device 210 generates a classification model based on the set of spectroscopic measurements and using an SVM classifier technique. For example, control device 210 trains the classification model to perform a determination of a type of compound (e.g., a type of meat) based on an unknown spectra. In this way, control device 210 generates a model for utilization in determining whether an unknown sample is Kosher (or, in another example, Halal or the like). As shown by reference number 540, control device 210 provides the classification model for loading to other control devices 210 (not shown) to permit the other control devices 210 to use other spectrometers 220 (not shown) to perform classifications of unknown samples (e.g., into Kosher or Non-Kosher groups).

As indicated above, FIG. 5 is provided merely as an example. Other examples are possible and may differ from what was described with regard to FIG. 5.

Figure 6:
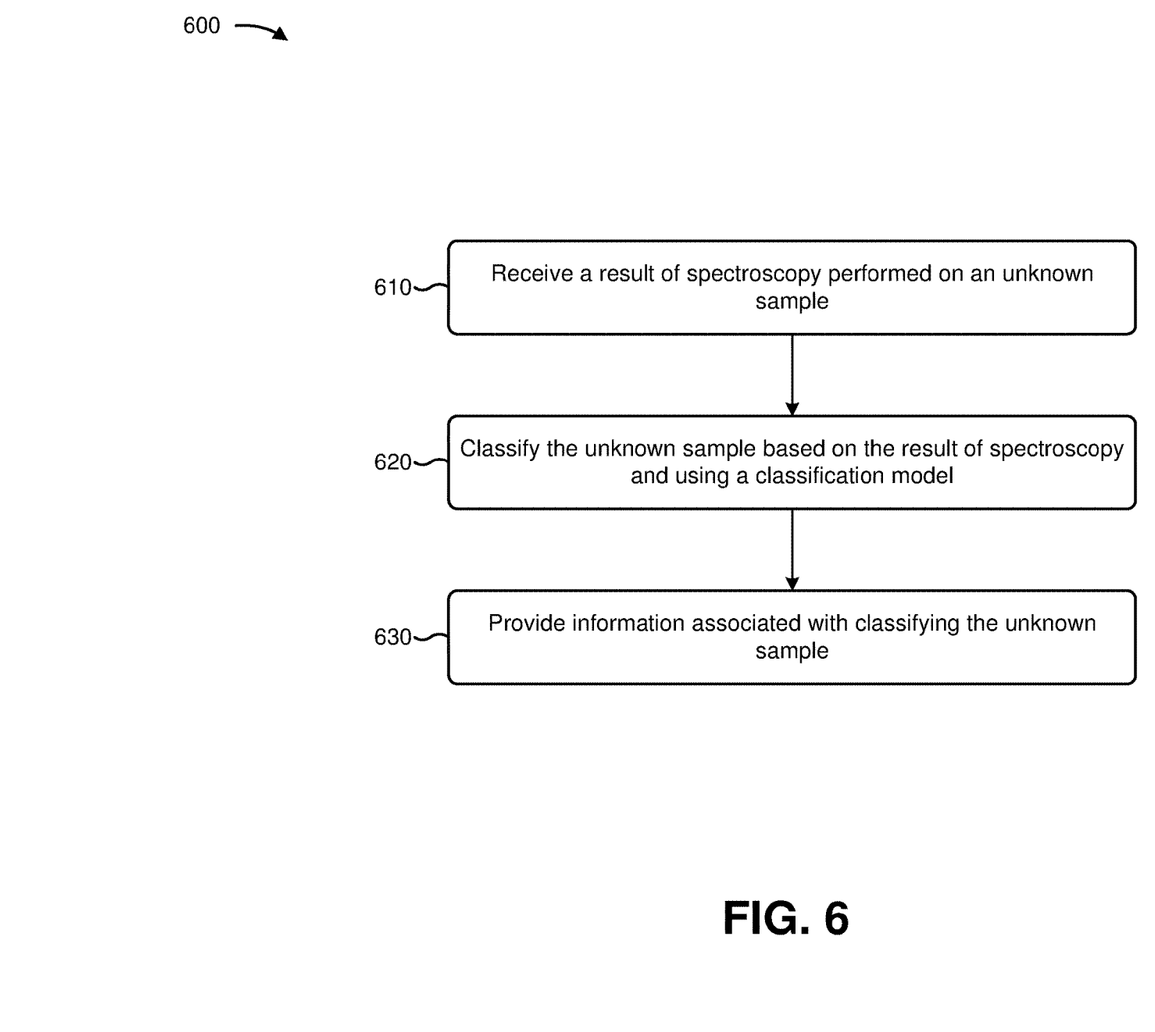
FIG. 6 is a flow chart of an example process for utilizing a classification model to categorize an unknown sample.

FIG. 6 is a flow chart of an example process 600 for utilizing a classification model to categorize an unknown sample. In some implementations, one or more process blocks of FIG. 6 may be performed by spectrometer 220. In some implementations, one or more process blocks of FIG. 6 may be performed by another device or a group of devices separate from or including spectrometer 220, such as control device 210.

As shown in FIG. 6, process 600 may include receiving a result of spectroscopy performed on an unknown sample (block 610). For example, control device 210 may receive the result of spectroscopy performed on the unknown sample. In some implementations, control device 210 may receive the result of spectroscopy based on spectrometer 220 performing spectroscopy without a prior request or instruction from control device 210. For example, a user of spectrometer 220 may cause spectrometer 220 to perform spectroscopy on an unknown sample and send the result of the spectroscopy to control device 210. In some implementations, control device 210 may receive the result of spectroscopy based on causing spectrometer 220 to perform spectroscopy. For example, control device 210 may transmit a request to perform a set of spectroscopic measurements of an unknown sample, and may receive information identifying a spectrum of the unknown sample as a result of the set of spectroscopic measurements. In some implementations, control device 210 may receive information identifying results of a set of spectroscopic measurements performed at multiple times, in multiple locations, and/or by multiple spectrometers 220.

Additionally, or alternatively, control device 210 may receive information identifying results of a set of spectroscopic measurements performed for multiple portions of the unknown sample. For example, control device 210 may receive a first result of spectroscopy from spectrometer 220 based on spectrometer 220 performing spectroscopy on a first portion of the unknown sample and a second result of spectroscopy based on spectrometer 220 performing spectroscopy on a second portion of the unknown sample. In this way, control device 210 may account for physical conditions that may affect the result of spectroscopy, local variations in the unknown sample that may affect the result of spectroscopy, or the like.

In some implementations, control device 210 may cause a first spectrometer 220 to perform a first spectroscopic measurement on a first portion of the unknown sample and may cause a second spectrometer 220 to perform a second spectroscopic measurement on a second portion of the unknown sample. In this way, control device 210 may reduce a quantity of time to perform multiple spectroscopic measurements of the unknown sample relative to causing all the spectroscopic measurements to be sequentially performed by a single spectrometer 220.

As further shown in FIG. 6, process 600 may include classifying the unknown sample based on the result of spectroscopy and using a classification model (block 620). For example, control device 210 may classify the unknown sample based on the result of spectroscopy and using the classification model. In some implementations, control device 210 may obtain the classification model. For example, control device 210 may obtain the classification model from a data structure, and may utilize the classification model to classify the unknown sample. In some implementations, control device 210 may generate another classification model based on the classification model, and may utilize the other classification model to classify the unknown sample. For example, when control device 210 obtains a global classification model generated based on a training set of samples, control device 210 may generate a local classification model associated with the unknown sample (e.g., using an SVM classifier technique) to improve an accuracy of classifying the unknown sample. In this case, control device 210 may classify the unknown sample using the local classification model.

In some implementations, control device 210 may classify the unknown sample into a particular group based on the classification model. For example, control device 210 may identify a particular type of meat (e.g., Halal beef shoulder) as a most likely match for the unknown sample based on the results of spectroscopy performed on the unknown sample and the classification model. In some implementations, control device 210 may identify one or more other groups to which the unknown sample may be classified. For example, control device 210 may determine a likelihood that the unknown sample is a member of a set of groups, and may select a threshold quantity of groups, one or more groups with a threshold likelihood, or the like as potential classifications for the unknown sample.

In some implementations, control device 210 may classify the unknown sample into a meta-group (e.g., Kosher or Non-Kosher or Halal or Non-Halal) based on classifying the unknown sample into one or more groups. For example, based on control device 210 identifying the particular group of the unknown sample (e.g., Halal beef shoulder), control device 210 may classify the unknown sample into a particular meta-group with a characteristic related to the particular group (e.g., a Halal meta-group of multiple types of Halal meat). In some implementations, control device 210 may aggregate multiple likelihoods for multiple groups to classify the unknown sample into a meta-group. For example, when control device 210 determines that the unknown sample is associated with a first likelihood of being in a first group (e.g., 94% for Halal beef shoulder), a second likelihood of being in a second group (e.g., 3% for Halal beef flank steak), and a third likelihood of being in a third group (e.g., 1% for Non-Halal pork loin), control device 210 may aggregate the first and second likelihoods to determine a fourth likelihood (e.g., 97% for Halal) relating to a first meta-group and may determine a fifth likelihood (e.g., 1% for Non-Halal) for a second meta-group based on the third likelihood. In another example, control device 210 may utilize another mathematical technique for aggregating multiple likelihoods. In this way, control device 210 utilizes an aggregation of information related to multiple classification groups (e.g., for which there may be less than a threshold quantity of samples associated with achieving a threshold level of accuracy) to determine a classification of the unknown sample relating to a characteristic of the multiple classification groups with the threshold level of accuracy.

As further shown in FIG. 6, process 600 may include providing information associated with classifying the unknown sample (block 630). For example, control device 210 may provide information associated with classifying the unknown sample. In some implementations, control device 210 may provide information identifying a class of the unknown sample. For example, control device 210 may provide information indicating that the unknown sample is associated with a particular group (e.g., Kosher beef flank steak, Non-Kosher pork loin, Halal beef sirloin, or Non-Halal veal tenderloin). In some implementations, control device 210 may provide information identifying a characteristic of a class of the unknown sample. For example, control device 210 may provide information indicating that the unknown sample is associated with a particular meta-group associated with a particular characteristic (e.g., a Kosher meta-group or a Non-Kosher meta-group or a Halal meta-group or a Non-Halal meta-group).

In some implementations, control device 210 may provide information identifying an accuracy of a classification. For example, control device 210 may provide information indicating that the unknown sample is classified to a particular group, a particular meta-group, or the like with a particular likelihood of accuracy. Additionally, or alternatively, control device 210 may provide information identifying a likelihood associated with another group. For example, control device 210 may indicate that there is a 95% likelihood that the unknown sample is associated with a first group (e.g., Kosher beef flank steak), a 4% likelihood that the unknown sample is associated with a second group (e.g., Kosher beef shoulder), and a 1% likelihood that the unknown sample is associated with a third group (e.g., Non-Kosher beef shoulder).

In some implementations, control device 210 may provide the information associated with classifying the unknown sample for display. For example, control device 210 may cause the information to be provided for display to a user via a user interface (e.g., of control device 210, spectrometer 220, or of another device to which control device 210 may transmit the information). In some implementations, control device 210 may store information associated with classifying the unknown sample. For example, control device 210 may store information identifying a classification of the unknown sample, a location at which the spectroscopy was performed, a photograph of the unknown sample, and/or other information relating to performing spectroscopy of the unknown sample. In this way, control device 210 may store information for use in determining whether the unknown sample is being fraudulently/negligently represented (e.g., as Kosher or as Halal).

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7A:
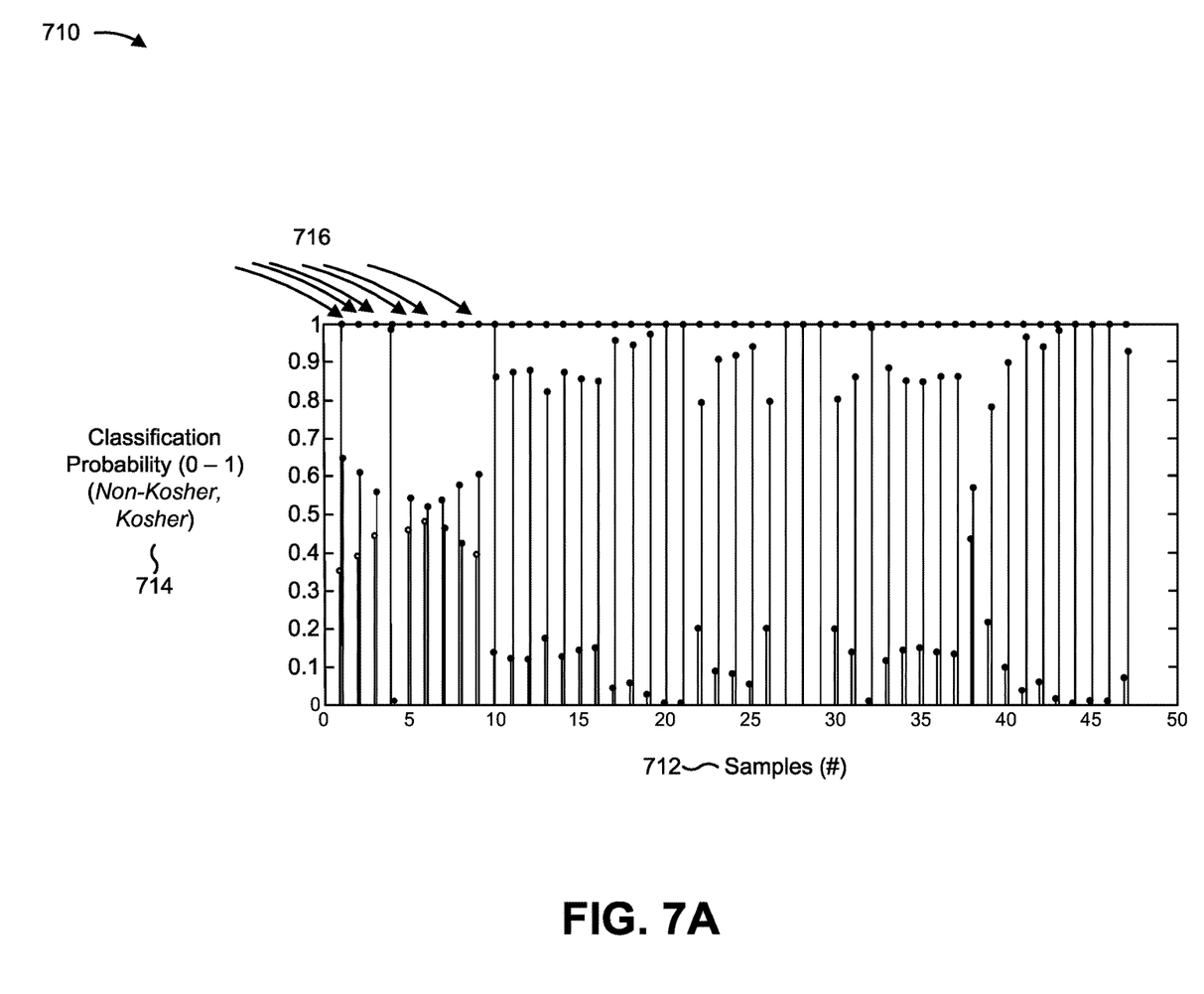
FIGS. 7A-7C are diagrams of an example implementation relating to the example process shown in FIG. 6.
Figure 7B:
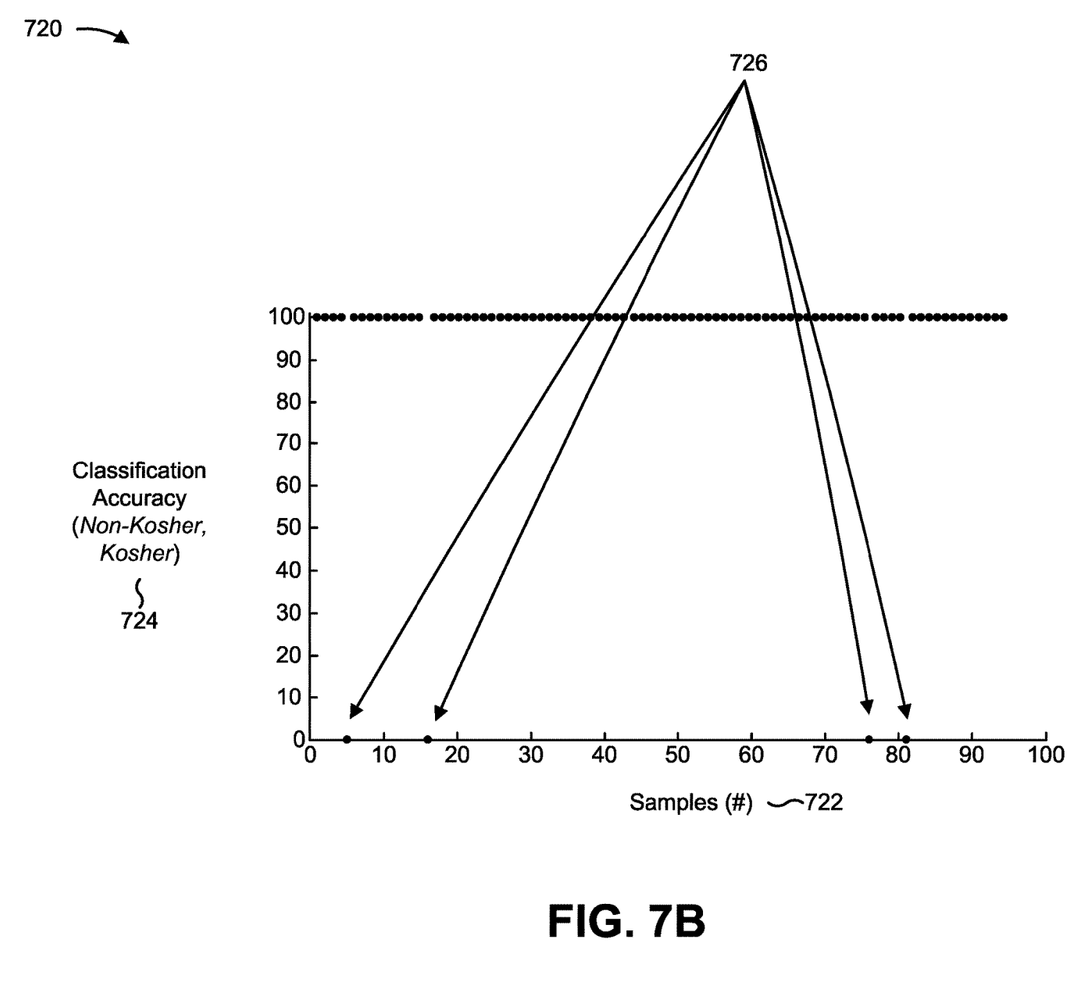
Figure 7C:
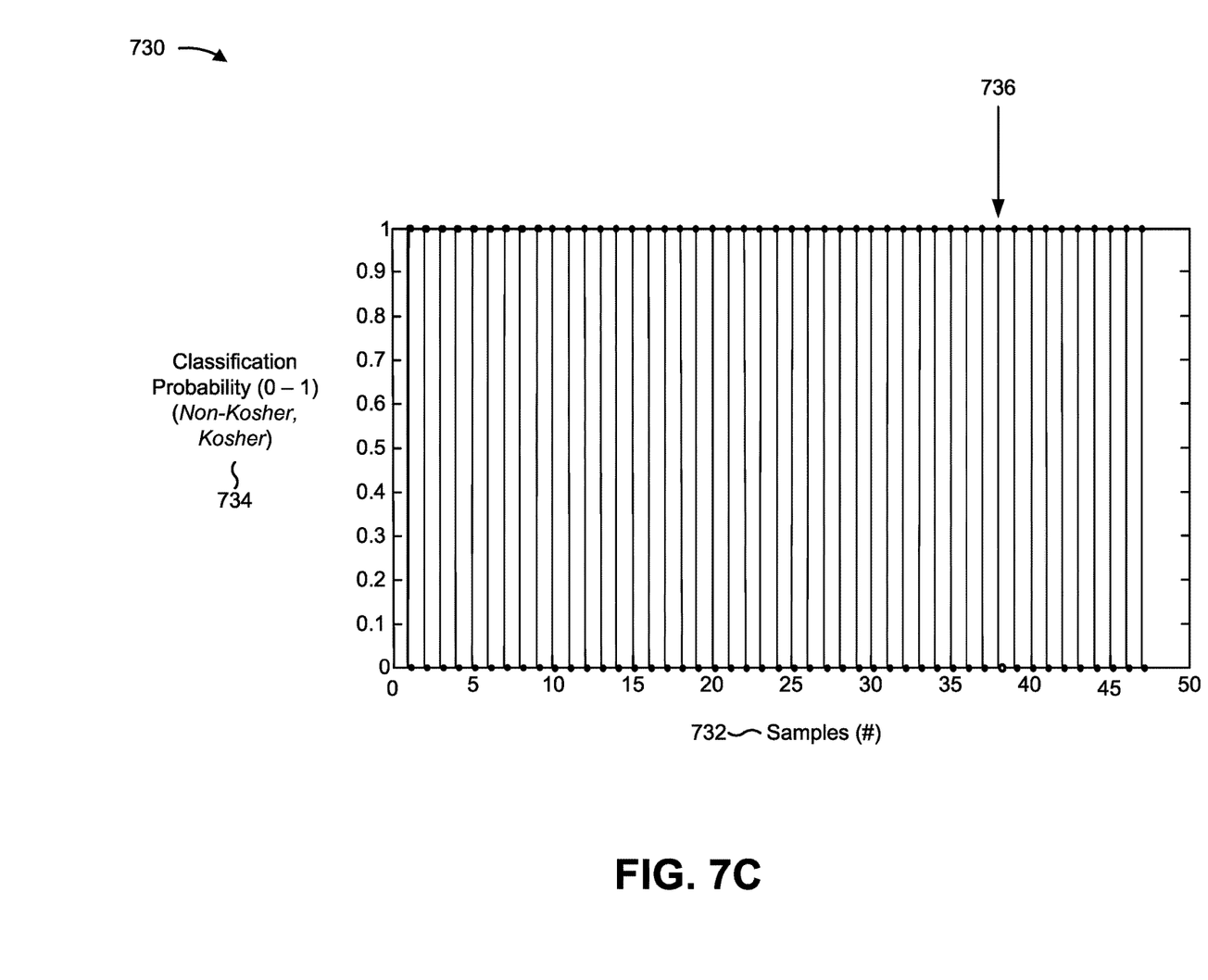

FIGS. 7A-7C are diagrams of an example implementation relating to example process 600 shown in FIG. 6. FIGS. 7A-7C show example results of identifying unknown samples using a set of classification models generated using a set of classifier techniques, from which a particular configuration for accurate identification of unknown samples can be selected.

As shown in FIG. 7A, an example chart 710 shows results of control device 210 performing a classification using results of spectroscopy from spectrometer 220. For example, control device 210 performs a set of classifications of a set of samples 712. In this case, control device 210 utilizes a T-odd P-even technique, using a wProb classification technique and an SVM-linear classifier. For example, control device 210 selects odd numbered samples as a training set and even numbered samples as a prediction set for utilization with the wProb classification technique. Based on generating a classification model using the odd-numbered samples, control device 210 performs a classification of the even numbered samples, and determines a classification probability for Kosher and Non-Kosher groups, as shown by reference number 714. As shown by reference number 716, a set of 6 classifications of a total of 47 classifications, performed by control device 210, are incorrect, resulting in an 87.23% prediction success rate.

As shown in FIG. 7B, an example chart 720 shows results of control device 210 performing another classification using results of spectroscopy from spectrometer 220. For example, control device 210 performs a set of classifications of a set of samples 722. In this case, control device 210 utilizes a one sample out technique, using a wProb classification technique and an SVM-linear classifier. For example, control device 210 selects a particular sample, generates a classification model based on results of spectroscopy corresponding to each other sample, and performs a classification of the sample based on the classification model. In this case, control device 210 determines a classification accuracy for Kosher and Non-Kosher groups, as shown by reference number 724 (e.g., a determination of whether a classification was accurate). As shown by reference number 726, a set of 4 classifications of a total of 94 classifications, performed by control device 210, are incorrect, resulting in a 95.74% prediction success rate.

As shown in FIG. 7C, an example chart 730 shows results of control device 210 performing another classification using results of spectroscopy from spectrometer 220. For example, control device 210 performs a set of classifications of a set of samples 732. In this case, control device 210 utilizes a T-odd P-even technique, using a wDecVals classification technique and an SVM-linear classifier. For example, control device 210 generates a classification model using odd numbered samples, performs a classification on even numbered samples based on the classification model to generate classifications of the even numbered samples, and uses a decision values technique to perform a prediction based on the generated classifications. In this case, control device 210 determines a classification probability for Kosher and Non-Kosher groups, as shown by reference number 724. As shown by reference number 726, a set of 1 classification of a total of 47 classifications, performed by control device 210, is incorrect, resulting in a 97.87% prediction success rate. In another example, similar results may be achieved for a wDecVals classification technique associated with a one sample out technique generation of a classification model with an SVM linear classifier. Based on decision values being associated with an improved classification accuracy for quantities of training set samples less than a threshold, control device 210 may be configured to use decision values to perform the classification based on spectroscopic measurements from spectrometer 220.

As indicated above, FIGS. 7A-7C are provided merely as an example. Other examples are possible and may differ from what was described with regard to FIGS. 7A-7C.

Control device 210 utilizes an SVM type of classifier with decision values to permit improved classification of samples for which a training set is less than a threshold size, such as less than 100 samples, less than 75 samples, less than 50 samples, less than 45 samples, or the like, relative to another type of classification technique. In this way, a user may be able to reliably use control device 210 and/or spectrometer 220 (e.g., integrated into a single package) to perform a spectroscopic measurement of an item of meat, and receive a determination (e.g., a numerical determination of a probability, a binary classification, etc.) via a user interface of the control device 210 and spectrometer 220 indicating whether the item of meat is Kosher or Halal. In this way, a user may be able to ensure that meat at a supermarket, a restaurant, or the like is accurately labeled with regard to being Kosher or Halal.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method comprising:
   receiving, by a device and from multiple spectrometers, information identifying results of a set of spectroscopic measurements performed on a training set,
      the training set including a set of samples not complying with particular dietary restrictions;
   generating, by the device and based on the results, a classification model to categorize an unknown sample; and
   providing, by the device, the classification model based on generating the classification model.

2. The method of claim 1, wherein the set of samples include a set of meats that control for differences in cortisol level for a particular type of meat.

3. The method of claim 1, wherein the training set further includes a different set of samples that comply with the particular dietary restrictions.

4. The method of claim 1, wherein the set of spectroscopic measurements are performed at different locations.

5. The method of claim 1, wherein the set of spectroscopic measurements are performed at multiple different times.

6. The method of claim 1, wherein generating the classification model comprises:
   utilizing a kernel function to generate the classification model.

7. The method of claim 1,
   wherein the device is a control device, and
   wherein providing the classification model comprises:
      providing the classification model to one or more other control devices associated with one or more other spectrometers.

8. The method of claim 1, wherein the training set includes one or more of:
   multiple types of meat, or
   multiple cuts of meat.

9. A device, comprising:
   one or more memories; and
   one or more processors, communicatively coupled to the one or more memories, configured to:
      receive, from multiple spectrometers, information identifying results of a set of spectroscopic measurements performed on a training set,
         the training set including a set of samples not complying with particular dietary restrictions;
      generate, based on the results, a classification model to categorize an unknown sample; and
      provide the classification model based on generating the classification model.

10. The device of claim 9, wherein the set of samples include a set of meats that control for differences in cortisol level for a particular type of meat.

11. The device of claim 9, wherein the training set further includes a different set of samples that comply with the particular dietary restrictions.

12. The device of claim 9, wherein the set of spectroscopic measurements are one or more of:
    performed at different locations, or
    performed at multiple different times.

13. The device of claim 9, wherein the one or more processors, when generating the classification model, are configured to:
    utilize a kernel function to generate the classification model.

14. The device of claim 9,
    wherein the device is a control device, and
    wherein the one or more processors, when providing the classification model, are configured to:
       provide the classification model to one or more other control devices associated with one or more other spectrometers.

15. The device of claim 9, wherein the training set includes one or more of:
    multiple types of meat, or
    multiple cuts of meat.

16. A non-transitory computer-readable medium storing a set of instructions, the set of instructions comprising:
    one or more instructions that, when executed by one or more processors of a device, cause the device to:
       receive, from multiple spectrometers, information identifying results of a set of spectroscopic measurements performed on a training set,
          the training set including a set of samples not complying with particular dietary restrictions;
       generate, based on the results, a classification model to categorize an unknown sample; and
       provide the classification model based on generating the classification model.

17. The non-transitory computer-readable medium of claim 16, wherein the set of samples include a set of meats that control for differences in cortisol level for a particular type of meat.

18. The non-transitory computer-readable medium of claim 16, wherein the training set further includes a different set of samples that comply with the particular dietary restrictions.

19. The non-transitory computer-readable medium of claim 16, wherein the set of spectroscopic measurements are one or more of:
    performed at different locations, or performed at multiple different times.

20. The non-transitory computer-readable medium of claim 16, wherein the training set includes one or more of:
    multiple types of meat, or
    multiple cuts of meat.

* * * * *